US00RE39847E

(19) United States
(12) Reissued Patent
Adjei et al.

(10) Patent Number: US RE39,847 E
(45) Date of Reissued Patent: Sep. 18, 2007

(54) METHOD OF TREATING A SYSTEMIC DISEASE

(75) Inventors: Akwete L. Adjei, Bridgewater, NJ (US); Anthony J. Cutie, Bridgewater, NJ (US)

(73) Assignee: Kos Life Sciences, Inc., Weston, FL (US)

(21) Appl. No.: 10/219,717

(22) Filed: Aug. 15, 2002

Related U.S. Patent Documents

Reissue of:
(64) Patent No.: 6,406,681
Issued: Jun. 18, 2002
Appl. No.: 09/642,437
Filed: Aug. 21, 2000

(51) Int. Cl.
*A61K 9/12* (2006.01)

(52) U.S. Cl. ..... 424/45; 424/46; 424/489; 128/200.14; 128/200.22

(58) Field of Classification Search ..... 424/45, 424/46, 489; 128/200.14, 200.23, 200.22, 128/898; 514/826, 2
See application file for complete search history.

(56) References Cited

U.S. PATENT DOCUMENTS 5,819,726 A * 10/1998 Rubsamen et al. .... 128/200.14
6,060,069 A * 5/2000 Hill et al. ..... 424/400
6,193,954 B1 * 2/2001 Adjei et al. ..... 424/45
6,261,539 B1 * 7/2001 Adjei et al. ..... 424/46
6,408,854 B1 * 6/2002 Gonda et al. ..... 128/898

OTHER PUBLICATIONS

Chavan and Dalby. Effects of rise in simulated inspiratory flow rate and carrier particle size on powder emptying from dry powder inhalers. AAPS PharmSci. 2000; 2 (2): article 10. Dol: 10.1208/ps020210.*

* cited by examiner

*Primary Examiner*—Johann Richter
*Assistant Examiner*—Mina Haghighatian
(74) *Attorney, Agent, or Firm*—Jonathan N. Provoost, Esq.; Karen P. Bechtold, Esq.

(57) ABSTRACT

A method of treating a systemic disease in a patient in need of such treatment is disclosed. The method comprising maintaining the inspiratory flow rate and volume of the patient to a certain value and then administering a medicament aerosol formulation to such patient.

7 Claims, No Drawings

METHOD OF TREATING A SYSTEMIC DISEASE

Matter enclosed in heavy brackets [ ] appears in the original patent but forms no part of this reissue specification; matter printed in italics indicates the additions made by reissue.

This application makes reference to U.S. application Ser. No. 09/158,369 filed on Sep. 22, 1998, *which issued as U.S. Pat. No. 6,136,294 on Oct. 24, 2000,* and 60/177,983 filed on Jan. 25, 2000, which are incorporated hereinto by reference in their entirety.

BACKGROUND OF THE INVENTION

1. Field of the Invention

This invention relates to method of treating a systemic disease, and more particularly, to a method which involves administering to a patient a medicinal aerosol spray from a pressurized metered dose inhaler, taking into consideration the inspiratory flow rate and inspiratory volume of the patient, dosing time, dosing period and duration of the administration.

2. Description of the Related Art

The treatment of a systematic disease with a medicament aerosol regimen is a standard practice. However, the practice employed is typically hit and miss in terms of a dosage regimen which is one which is maximized in its effect. What is needed and desired is a method of treating a systemic disease, e.g. diabetes, immune deficiency, asthma, pain, etc., taking into consideration the critical parameters of application.

SUMMARY OF THE INVENTION

This invention relates to method of treating a systemic disease in a patient, and more particularly, treating such disease with a medicinal aerosol.

DETAILED DESCRIPTION OF THE INVENTION

This invention involves a method of treating a systemic disease, e.g. diabetes, immune deficiency, asthma, pain, etc., in a patient, e.g. a human being or another animal, with a medicament or drug aerosol which comprises (a) the selected medicament and (b) a suitable fluid or propellant, (c) a metering device, and (d) a dose timing element. A suitable medicament includes therapeutic categories of drugs or medicaments such as cardiovascular drugs, antiallergics, antihistamines, antitussives, antifungals, antivirals, antibiotics, pain medicaments, antiinflammatories, steroids; biotherapeutics, including peptides, proteins, oligonucleotides, and gene vectors.

Other medicaments delivered via the airways for treating localized lung disease as well as drugs that may be delivered in aerosolized form for uptake into the systemic circulation of the patient being treated, e.g. a human being or another animal, include asthma drugs, like β-agonists, catecholamines, cyclic corticosteroid drugs, antihistamines, antcholinergics and other brochodilators; systematically acting drugs like pain management compounds, such as morphine and fentanyl; proteins and peptides, such as insulin, amylin, growth hormone, octreotide and leuprolide, and anti-migraine drugs like ergotamine.

As used herein the following terms are defined as follows.

The terms "peptide," "polypeptide", "oligopeptide" and "protein" shall be used interchangeably when referring to peptide, or protein drugs and shall not be limited as to any particular molecular weight peptide sequence or length, field of bioactivity or therapeutic use unless specifically stated.

A suitable medicament to which the subject invention is directed includes a peptide, polypeptide or protein biotherapeutic medicament ranging from 0.5 K Dalton to 150 K Dalton in molecular size. In particular, the peptide, polypeptide, or protein biotherapeutic medicament includes diabetic aids; such as insulin and insulin analogs; amylin; glucagon; surfactants; immunomodulating peptides such as cytokines, chemokines, lymphokines; interleukins, such as taxol, interleukin-1, interleukin-2, and interferons; erythropoetins; thrombolytics and heparins; anti-proteases, antitrypsins and amiloride; rhDNase; antibiotics and other antiinfectives; hormones; and growth factors, such as parathyroid hormones, LH-RH and GnRH analogs; nucleic acids; DDAVP; calcitonins; cyclosporins; ribavirin; enzymes; heparins; hematopoietic factors; cyclosporins; vaccines; immunoglobulins; vasoactive peptides; antisense agents; genes, olignucleotide, and nucleotide analogs.

The term "diabetic aid includes natural, synthetic, semisynthetic and recombinant medicaments, such as activin, glucagon, insulin, somatostatin, proinsulin, amylin, and the like.

The term "insulin" shall be interpreted to encompass insulin analogs, natural extracted human insulin, recombinantly produced human insulin, insulin extracted from bovine and/or porcine sources, recombinantly produced porcine and bovine insulin and mixtures of any of these insulin products. The term is intended to encompass the polypeptide normally used in the treatment of diabetics in a substantially purified form but encompasses the use of the term in its commercially available pharmaceutical form, which includes additional excipients. The insulin is preferably recombinantly produced and may be dehydrated (completely dried) or in solution.

The terms "insulin analog," "monomeric insulin" and the like are used interchangeably herein and are intended to encompass any form of "insulin" as defined above, wherein one or more of the amino acids within the polypeptide chain has been replaced with an alternative amino acid and/or wherein one or more of the amino acids has been deleted or wherein one or more additional amino acids has been added to the polypeptide chain or amino acid sequences, which act as insulin in decreasing blood glucose levels. In general, the term "insulin analogs" of the present invention include "insulin lispro analogs," as described in U.S. Pat. No. 5,547,929, incorporated hereinto by reference in its entirety; insulin analogs including LysPro insulin and humalog insulin, and other "super insulin analogs", wherein the ability of the insulin analogs to affect serum glucose levels is substantially enhanced as compared with conventional insulin a swell as hepatoselective insulin analogs which are more active in the liver than in adipose tissue. Preferred analogs are monomeric insulin analogs, which are insulin-like compounds used for the same general purpose as insulin, such as insulin lispro, i.e., compounds which are administered to reduce blood glucose levels.

The term "amylin" includes natural human amylin, bovine, porcine, rat, rabbit amylin, as well as synthetic, semi-synthetic or recombinant amylin or amylin analogs including pramlintide and other amylin agonists, as disclosed in U.S. Pat. Nos. 5,686,411 and 5,854,215, both of which are incorporated hereinto by reference in their entirety.

The term "immunomodulating proteins" include cytokines, chemokines, lymphokines complement components, immune system accessory and adhesion molecules and their receptors of human or non-human animal specificity. Useful examples include GM-CSF, IL-2, IL-12, OXO40, OXO40L (gp34), lymphotactin, CD40, CD40L. Useful examples include interleukins, for example interleukins 1 to 15; interferons alpha, beta or gamma; tumour necrosis factor, granulocyte-macrophage colony stimulating factor (GM-CSF), macrophage colony stimulating factor (M-CSF), granulocyte colony stimulating factor (G-CSF), chemokines, such as neutrophil activating protein (NAP); macrophage chemoattractant and activating factor (MCAF), RANTES, microphage inflammatory peptides, MIP-1a and MIP-1b, complement components and their receptors, or an accessory molecule, such as B7.1, B7.2, ICAM-1, 2 or 3 and cytokine receptors. OXO40 and OXO40-ligand (gp34) and further useful examples of immunomodulatory proteins. Immunomodulatory proteins can for various purposes be of human or non-human animal specificity and can be represented, for present purposes, as the case may be and as may be convenient, by extracellular domains and other fragments with the binding activity of the naturally occurring proteins, and mutants thereof, and their fusion proteins with other polypeptide sequences, e.g. with immunoglobulin heavy chain constant domains. Where nucleotide sequences encoding more than one immunomodulating protein are inserted, they can, for example, comprise more than one cytokine or a combination of cytokines and accessory/adhesion molecules.

The term "interferon" or "IFN" as used herein means the family of highly homologous species-specific proteins that inhibit viral replication and cellular proliferation and modulate immune response. Interferons are grouped into three classes based on their cellular origin and antigenicity, namely, alipha-interferons (leukocytes), beta-interferon (fibroblasts) and gamma-interferons (immunocompetent cells). Recombinant forms and analogs of each group have been developed and are commercially available. Subtypes in each group are based on antigenic/structural characteristics. At least 24 interferon alphas (grouped into subtypes A through H) having distinct amino acid sequences have been identified by isolating and sequencing DNA encoding these peptides. Reference is made to Viscomi, 1996 Biotherapy 10:59–86, the contents of which are incorporated by reference hereinto in its entirety. The terms "alpha.-interferon", "alpha interferon", "interferon alpha", "human leukocyte interferon" and "IFN" are used interchangeably herein to describe members of this group. Both naturally occurring and recombinant alpha interferons, including consensus interferon such as that described in U.S. Pat. No. 4,897,471, the contents of which are incorporated hereinto by reference in its entirety, may be used in the practice of the invention. Human leukocyte interferon prepared in this manner contains a mixture of human leukocyte interferons having different amino acids sequences. Purified natural human alpha interferons and mixtures thereof which may be used in the practice of the invention include but are not limited to Sumiferon RTM interferon alpha-n1 available from Sumitomo, Japan; Welfferong interferon alpha-n1 (Ins) available from Glaxo-Wellcome Ltd., London, Great Britain; and Alferon RTM interferon alpha-n3 available from the Purdue Frederick Co., Norwalk, Conn.

The term "erythropoietin" applies to synthetic, semi-synthetic, recombinant, natural, human, monkey, or other animal or microbiological isolated polypeptide products having part or all of the primary structural conformation (i.e., continuous sequence of amino acid residues) and one or more of the biological properties (e.g., immunological properties and in vivo and in vitro biological activity) of naturally-occurring erythropoietin, including allelic variants thereof. These polypeptides are also uniquely characterized by being the product of procaryotic or eurcaryotic host expression (e.g., by bacterial, yeast and mammalian cells in culture) of exogenous DNA sequences obtained by genomic or cDNA cloning or by gene synthesis. Products of microbial expression in vertebrate (e.g., mammalian and avian) cells may be further characterized by freedom from association with human proteins or other contaminants which may be associated with erythropoietin in its natural mammalian cellular environment or in extracellular fluids such as plasma or urine. The products of typical yeast (e.g., Saccaromyces cerevisiae) or procaryote (e.g., E. coli) host cells are free of association with any mammalian proteins. Depending upon the host employed, polypeptides of the invention may be glycosylated with mammalian or other eucaryotic carbohydrates or may be nonglycosylated. Polypeptides of the invention may also include an initial methionine amino acid residue (at position-1). Novel glycoprotein products of the invention include those having a primary structural conformation sufficiently duplicative of that of a naturally-occurring (e.g., human) erythropoietin to allow possession of one or more of the biological properties thereof and having an average carbohydrate composition which differs from that of naturally-occurring (e.g., human) erythropoietin.

The terms "heparins" and "thrombolytics" include anti-clotting factors such as heparin, low molecular weight heparin, tissue plasminogen activator (TPA), urokinase (Abbokinase) and other factors used to control clots.

The terms "anti-proteases" and "protease-inhibitors" are used interchangeably and apply to synthetic, semi-synthetic, recombinant, naturally-occurring or non-naturally occurring, soluble or immobilized agents reactive with receptors, or act as antibodies, enzymes or nucleic acids. These include receptors which modulate a humoral immune response, receptors which modulate a cellular immune response (e.g., T-cell receptors) and receptors which modulate a neurological response (e.g., glutamate receptor, glycine receptor, gamma-amino butyric acid (GABA) receptor). These include the cytokine receptors (implicated in arthritis, septic shock, transplant rejection, autoimmune disease and inflammatory diseases), the major histocompatibility (MHC) Class I and II receptors associated with presenting antigen to cytotoxic T-cell receptors and/or T-helper cell receptors (implicated in autoimmune diseases) and the thrombin receptor (implicated in coagulation, cardiovascular disease). Also included are antibodies which recognize self-antigens, such as those antibodies implicated in autoimmune disorders and antibodies which recognize viral (e.g., HIV, herpes simplex virus) and/or microbial antigens.

The terms "hormones" and "growth factors" include hormone releasing hormones such as growth hormone, thyroid hormone, thyroid releasing hormone (TRH), gonadotropin-releasing hormone (GnRH), leuteinizing hormone, leuteininzing hormone-releasing hormone (LHRH, including the superagonists and antagonists, such as leuprolide, deltirelix, gosorelin, danazol, etc.) sourced from natural, human, porcine, bovine, ovine, synthetic, semi-synthetic, or recombinant sources. These also include somatostsatin analogs such as octreotide (Sandostatin). Other agents in this category of biotherapeutics include medicaments for uterine contraction (e.g., oxytocin), diuresis (e.g., vasopressin), neutropenia (e.g., GCSF), medicaments of respiratory disorders (e.g. superoxide dismutase), RDS (e.g., surfactants, optionally including apoproteins), and the like.

The terms "enzymes" include recombinant deoxyribonuclease such as DNAse (Genentech) proteases (e.g., serine proteases such as trypsin and thrombin), polymerase (e.g., RNA polymerases, DNA polymerases), reverse transcriptases and kinases, enzymes implicated in arthritis, osteoporosis, inflammatory diseases, diabetes, allergies, organ transplant rejection, oncogene activation (e.g., dihydrofolate reductase), signal transduction, self-cycle regulation, transcription, DNA replication and repair.

The term "nucleic acids" includes any segment of DNA or RNA containing natural or non-naturally occurring nucleosides, or other proteinoid agents capable of specifically binding to other nucleic acids or oligonucleotides via complementary hydrogen-bonding and also are capable of binding to non-nucleic acid ligates. In this regard, reference is made to Bock, L., et al., Nature 355:564–566 (1992) which reports inhibition of the thrombin-catalyzed conversion of fibrinogen to fibrin using aptamer DNA.

Examples of biological molecules for which lead molecules can be synthesized and selected and combined in accordance with the invention include, but are not limited to, agonsits and antagonists for cell membrane receptors, neutrotrasmitters, toxins, and venoms, viral epitopes, hormones, opiates, steroids, peptides, enzyme substrates and inhibitors, cofactors, drugs, lectins, sugars, oligonucleotides, nucleic acids, oligosaccharides, lipis, proteins, and analogs of any of the foregoing molecules.

The term "analog" refers to a molecular, which shares a common functional activity with the molecule to which it is deemed to be comparable and typically shares common structural features as well.

The term "recombinant" refers to any type of cloned biotherapeutic expressed in procaryotic cells or a genetically engineered molecule, or combinatorial library of molecules which may be further processed into another state form a second combinatorial library, especially molecules that contain protecting groups which enhance the physiochemical, pharmacological, and clinical safety of the biotherapeutic agent.

The term "vaccines" refers to therapeutic compositions for stimulating humoral and cellular immune responses, either isolated, or through an antigen presenting cells, such as an activated dendritic cell, that is able to activate T-cells to produce a multivalent cellular immune response against a selected antigen. The potent antigen presenting cell is stimulated by exposing the cell in vitro to a polypeptide complex. The polypetpide complex may comprise a dendritic cell-binding protein and a polypeptide antigen, but preferably, the polypeptide antigen is either a tissue-specific tumor antigen or an oncogene gene product. However, it is appreciated that other antigens, such as viral antigens can be used in such combination to produce immunostimulatory responses. In another preferred embodiment, the dendritic cell-binding protein that forms part of the immunostimulatory polypeptide complex is GM-CSF. In a further preferred embodiment, the polypeptide antigen that forms part of the complex is the tumor-specific antigen prostatic acid phosphatase. In still other preferred embodiments, the polypeptide antigen may be any one of the oncogene product peptide antigens. The polypetpide complex may also contain, between the dendritic cell-binding protein and the polypeptide antigen, a linker peptide. The polypeptide complex may comprise a dendritic cell-binding protein covalently linked to a polypeptide antigen, such polypeptide complex being preferably formed from a dendritic cell binding protein, preferably GM-CSF; and a polypeptide antigen. The polypeptide antigen is preferably a tissue-specific tumor antigen such as prostatic acid phosphatase (PAP), or an oncogene product, such as Her2, p21RAS, and p53; however, other embodiments, such as viral antigens, are also within the scope of the invention.

The term "immunoglobulins" encompasses polypeptide oligonucleotides involved in host defense mechanisms, such as coding and encoding by one or more gene vectors, conjugating various binding moieties of nucleic acids in host defense cells, or coupling expressed vectors to aid in the treatment of a human or animal subject. The medicaments included in this class of polypeptides include IgG, IgE, IgM, IgD, either individually or in a combination with one another.

The selected medicament is preferably in particulate form for treatment of systemic disease via aerosol delivery. Accordingly, the drug or medicament should have a diameter ranging from about one to about 7 micrometers.

The biotherapeutic medicament is present in the formulations in a therapeutically effective amount, that is, an amount such that the biotherapeutic medicament can be incorporated into an aerosol formulation such as a dispersion, aerosol, via oral inhalation or nasal inhalation, and cause its desired therapeutic effect, typically preferred with one dose, or through several doses. The drug is typically administered as an aerosol from a conventional valve, e.g. a metered dose valve, through an aerosol adapter also known as an actuator.

The term "dosing interval" shall be interpreted to mean the period during which administration of the selected medicament may be given to a patient in need thereof by the intrapulmonary route of administration which period may encompass preferably from about every 3 to about 4 hours in a day for a suitable dosing time of about 200 to about 2000 milliseconds during the patient's inspiratory cycle.

The term "inspiratory cycle" is used herein to refer to the total time used by a patient to breath in air until just before exhaling commences, i.e., the time taken to ventilate a persons's lungs completely.

The term "dosing timing element" as used herein shall be interpreted to mean a timer, a dose counter, time measuring device, or a time indicator which when incorporated into the aerosol device enables dose tracking, compliance monitoring, and/or dose triggering to a patient during administration of the aerosol medicament.

The term "dosing time" as used herein shall be interpreted to mean the timing in a patient's inspiratory cycle during which as ingle spray of formulation may be released to the patient via the intrapulmonary route of administration which event may commence at about 200 milliseconds to 2000 milliseconds into the inspiratory cycle of the said patient, which time may also conclude before exhalation commences.

The term "dosing period" as used herein shall be interpreted to encompass one or more releases of aerosolized medication over a period of time as required by the medicament's pharmacologic action.

The term "amount" as used herein refers to a quantity or to a concentration as appropriate to the context. The amount of a drug that constitutes a therapeutically effective amount varies according to factors such as the potency of the particular biotherapeutic medicament, the route of administration of the formulation, and the mechanical system used to administer the formulation. A therapeutically effective amount of a particular drug can be selected by those of ordinary skill in the art with due consideration of such factors. Preferably a suitable therapeutically effective amount of biotherapeutic medicament will be from about 0.00001 parts by weight to about 5 parts by weight based on 100 parts by weight of the fluid or propellant carrier selected.

A suitable fluid carrier is one that carries and transports the particles having a selected medicament and includes air, a hydrocarbon such as n-butane, propane, isopentane, etc. or a propellant. A suitable propellant is any fluorocarbon, e.g. a 1–6 hydrogen containing fluorocarbon (such as $CHF_2CHF_2$, $CF_3CH_2F$, $CH_2F_2CH_3$ and $CF_3CHFCF_3$), a perfluorocarbon, e.g. a 1–4 carbon perfluorocarbon, (such as $CF_3CF_3$, $CF_3CF_2CF_3$); or any mixture of the foregoing, having a sufficient vapor pressure to render them effective as propellants. Some typical suitable propellants include conventional chlorofluorocarbon (CFC) propellants such as propellants 11, 12 and 114 or a mixture thereof. Non-CFC propellants such as 1,1,1,2-tetrafluoroethane (Propellant 134a), 1,1,1,2,3,3,3-hepatfluoropropane (Propellant 227) or a mixture thereof are preferred. The fluid or propellant is preferably present in an amount sufficient to propel a plurality of selected doses of drug in the form of particles from an aerosol canister when such is employed.

Optionally, a suitable stabilizer is selected. A suitable stabilizer includes (1) an amino acid selected from (a) a monoamino carboxylic acid of the formula, $H_2N$—R—COOH (I), (b) a monoamino dicarboxylic acid of the formula, $H_2N$—$R(COOH)_2$(II) and (c) a diamino monocarboxylic acid of the formula $(H_2N)_2$—RCOOH(III), where R is a straight or branched alkyl radical of from 1 to 22 carbon atoms, which can be mono or poly-substituted with moieties such as sulfide (—S—), oxide (—O—), hdyroxyl (—OH), amide (—NH), sulfate (—SO4); aryl of the formula

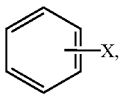

where X is hydrogen, halogen (F, Cl, BR, I), alkyl of 1 to 6 carbon atoms, alkoxy of 1 to 6 carbon atoms, hydroxy and nitro; and heterocyclic, such as thienyl, furyl, pyranyl, imidazolyl, pyrrolyl, thizolyl, oxazolyl, pyridyl, and pyrimidinyl compounds; (2) a derivative of the amino acid selected from the (a) acid addition salts of the amino group, obtained from inorganic acids, such as hydrochloric, hydrobomic, sulfuric, nitric, phosphoric, and perchloric acids, as well as organic acids, such as tartaric, citric, acetic, succinic, maleic, fumaric, oxalic acids; (b) amides of the carboxylic acid group, e.g., glutamine, di-peptides, e.g. salts and esters of oxidized and unoxidized L-cysteinylglycine, gamma-L-glutamyl-L-cysteine, N-acetyl-L-cysteine-glycine, either conjugated, unconjugated or polymeric forms of L-gly-L-Glu and L-Val-L-Thr, L-aspartyl-L-phenylalanine, muramyl, dipeptides, nutrients such as L-tyrosyl-L-tyrosine, L-alanyl-L-tyrosine, L-arginyl-L-tyrosine, L-tyrosyl-L-argine, N-Cbz-L-Leu-L-Leu-OCH and its salts or esters, glycyl-glycine, N-acetyl-L-aspartate-L-blutamate (NAAG), etc.; and tripeptides, e.g. oxidized and unoxidized gamma-L-glutamyl-L-cysteinylglycine; muramyl tripeptides, etc.; (c) esters of the carboxylic acid group obtained from aliphatic straight or branched chain alcohols of from 1 to 6 carbon atoms, e.g. L-aspartyl-L-phehylalanine methylester (Aspartame®), (3) an ether of any of the foregoing; (4) a hydrate or semi-hydrate of any of the foregoing and (5) a mixture of the amino acid and the derivative of the amino acid.

Suitable amino acids of the inventive formula include glycine, alanine, valine, leucine, isoleucine, leucylalanine, methionine, threonine, isovaline, phenylalanine, tyrosine, serine, cysteine, N-acetyl-L-cysteine, histidine, tryptophan, proline, and hydroxyproline, e.g. trans-4-hydroxy proline. Compounds of the formula II include aspartic acid, and glutamid acid, compounds of the formula (III) include arginine, glutamine, lysine, hydroxylysine, ornithine, asparagine, and citrulline.

A fluid or aerosol formulation preferably comprises the protective colloid stabilizer in an amount effective to stabilize the formulation relative to an identical formulation not containing the stabilizer, such that the drug does not settle, cream or flocculate after agitation so quickly as to prevent reproducible dosing of the drug. Reproducible dosing can be achieved if the formulation retains a substantially uniform drug concentration for about fifteen seconds to about five minutes after agitation.

For optimal functional and therapeutic performance of the aerosol formulation, as an aerosol suspension, the stabilizer is present either as a coarse carrier (e.g., 20–90 μm) or as a finely microionized powder, ≦10 μm in diameter. In either case, reproducible drug dosiometry is obtained without the need to qualify the inspiratory maneuver of the patient. Accordingly, excellent dose uniformly is obtained at tidal flows up to 2 liters, or at inspiratory flow rates of as low as 15 liters per minute to about 90 liters per minute.

Alternatively, optionally, a second suitable stabilizer is selected instead of the first stabilizer. A second suitable stabilizer is a "water addition". As used herein a "water addition" is an amount of water which (1) is added, either initially with other components of the described aerosol formulation, e.g. medicament associated with the polymeric construct as part thereof or encapsulated therein, and fluid carrier, or after the other components, e.g. medicament, fluid carrier, are combined and processed, (2) is in addition to the water which is always present and which develops during processing and/or storage of the aerosol formulation, i.e. "developed" or "nascent" formulation water, and (3) is present in an amount which further stabilizes a medicinal aerosol formulation, e.g. rosiglitazone maleate, having nascent formulation water.

An aerosol formulation preferably comprises the water addition in an amount effective to more effectively stabilize the formulation relative to an identical formulation not containing the water addition, i.e. containing only nascent formulation water, such that the drug e.g., an insulin containing construct, does not settle, cream or flocculate after agitators so quickly as to prevent reproducible dosing of the drug. Reproducible dosing can be achieved if the formulation retains a substantially uniform drug concentration for about fifteen seconds to about five minutes after agitation.

The particular amount of stabilizer that constitutes an effective amount is dependent upon the particular stabilizer, the particular propellant, and on the particular drug used in the formulation. It is therefore not practical to enumerate specific effective amounts for use with specific formulations of the invention, but such amounts can readily be determined by those skilled in the art with due consideration of the factors set forth above. Generally, however, the stabilizer can be present in a formulation in an amount from about 0.001 parts per million to about 200,000 parts per million, more preferably about 1 part per million to about 10,000 parts per million, most preferably from about 10 parts per million to about 5,000 parts per million of the total formulation.

It has surprisingly been found that the formulation of the invention is stable without the necessity of employing a cosolvent, such as ethanol, or surfactants. However, further components, such as conventional lubricants or surfactants, co-solvents, ethanol, etc., can also be present in an aerosol formulation of the invention in suitable amounts readily determined by those skilled in the art. In this regard, reference is made to U.S. Pat. No. 5,225,183, which is incorporated by reference hereinto in its entirety.

Generally the formulations of the invention can be prepared by combining (i) the biotherapeutic medicaments or drug in an amount sufficient to provide a plurality of therapeutically effective doses of the biotherapeutics; (ii) if necessary, adding an appropriate suspension stabilizer in an amount effective to stabilize each of the formulations; (iii) dispersing the stabilized biotherapeutic medicament in an appropriate fluid or propellant in an amount sufficient to propel a plurality of doses, e.g. from an aerosol canister; and (iv) adding any further optional components, e.g. ethanol as a cosolvent; and homogenizing the components until a uniform dispersion is achieved. The components can be dispersed using a conventional mixer or homogenizer, by shaking, or by ultrasonic energy. The components can also be dispersed using a bead mill or a microfluidizer. Bulk formulations can be transferred to smaller individual aerosol vials by using valve to valve transfer methods, pressure filling or by using conventional cold-fill methods. It is not required that a stabilizer used in a suspension aerosol formulation be soluble in the propellant. Those that are not sufficiently soluble can be coated onto the drug particles in an appropriate amount and the coated particles can then be incorporated in a formulation as described above.

Aerosol canisters equipped with conventional valves, preferably metered dose valves, can be used to deliver the formulation of the invention. It has been found, however, that selection of appropriate valve assemblies for use with aerosol formulations is dependent upon the particles stabilizer and other adjuvant used (if any), on the propellant, and on the particular drug being used. Conventional neoprene and buna valve rubbers used in metered dose valves for delivering conventional CFC formulations often have less than optimal valve delivery characteristics and ease of operation when used with formulations containing HFC-134a or HFC-227. Therefore certain formulations of the invention are preferably dispersed via a valve assembly wherein the diaphragm is made of a nitrile rubber such as DB-218 (American Gasket and Rubber, Schiller Park, Ill.) or an EPDM rubber such as Vistalon™ (Exxon), Royalene™ (UniRoyal), bunaEP (Bayer). Also suitable are diaphragms fashioned by extrusion, injection molding or compression molding from a thermoplastic elastomeric material such as FLEXOMER™ GERS 1085 NT polyolefin (Union Carbide).

Conventional aerosol canisters, coated or uncoated, anodized or unanodized, e.g., those of aluminum, glass, stainless steel, polyethylene terephthalate, and coated canisters or cans with epon, epoxy, etc., can be used to contain a formulation of the invention. The contents of the canister can be introduced into the canister by either the cold fill process or the pressure fill process. These processes as well as other processes, devices, etc., are described in "Metered Dose Inhaler Technology," Tol. S. Purewal et al., Ed., Interpharm Press Inc., 1998, which is incorporated by reference hereinto in its entirety.

Conventional nebulizer systems can be employed the formulations of this invention, as well as by powder aerosols.

The formulation of the invention may be administered via the intrapulmonary or intranasal route using a dose timing device. The timing device may be mechanically or electronically integrated into the activation mechanism of the metered dose valve such that the aerosol medicament is released at fixed time during the inspiratory cycle of the patient.

The formulation of the invention can be delivered to the respiratory tract and/or lung of the patient to be treated, e.g. a human being or other animal, by oral inhalation in order to effect bronchodilation or in order to treat a condition susceptible of treatment by inhalation, e.g., asthma, chronic obstructive pulmonary disease.

The formulation of the invention can also be delivered to the lung in order for the biotherapeutic agent to be delivered at measured rates to the systemic circulation for treatment of diseases elsewhere in the body, e.g., diabetes, hormone replacement, cancer, erythropoiesis, infection, or for immune protection such as achievable with vaccines.

The formulations of the invention can also be delivered by nasal inhalation in order to treat, for example, allergic rhinits, rhinits, (local) or diabetes (systemic), or they can be delivered via topical (e.g. buccal) administration in order to treat, e.g., angina or local infection.

he formulations of the invention can be used to treat systemic disease in a patient e.g. human being or another animal, suffering from such diseases. Initially, the inspiratory flow rate of the patient is established and maintained at a range of from 0.05 to about 2.0 liters per second. This is accomplished by allowing drug administration to be carried out under the patient's normal tidal flow. Additionally, each dose administered is timed to commence at about 200 milliseconds to 200 milliseconds during the inspiratory cycle.

having established and maintained these parameters in the patient, the medicinal aerosol formulation comprising an effective amount, e.g. about 0.00001 parts to about 5 parts by weight to about 100 parts by weight of the carrier, and the selected fluid carrier is administered to the patient at the suitable dosing time for the suitable dosing period, for about 1 to about 4 sprays of the aerosol formulation every 3 to 4 hours in a day in a dosing time of preferably about 200 to about 2000 milliseconds, e.g. about 500 to about 800 milliseconds.

We claim:

1. A method of treating a systemic disease in a patient in need thereof, which consists essentially of:

(a) maintaining the inspiratory flow rate in the patient in a range of about 0.05 to about 2 liters per second and the inspiratory volume of the patient in the range of about 0.1 to about 5 liters; and (b) administering to the patient a medicinal aerosol formulation comprising (a') a medicament present in an effective amount[; and], (b') a fluid propellant carrier for carrying said transporting said medicament *to the patient* at a *suitable* dosing time of about 200 to about 2000 milliseconds for a suitable dosing period *and*

(*c'*) *a stabilizer selected from the group consisting of an amino acid, a derivative thereof, a water addition stabilizer and a mixture of any of the foregoing*.

[2. The method as defined in claim 1 wherein said suitable dosing time comprises about 200 to about 2000 milliseconds.]

3. The method as defined in claim 1 [or claim 2] wherein said suitable dosing period comprises about 1 to about 4 sprays of the aerosol formulation every 3 to 4 hours.

4. The method as defined in claim 3 wherein said effective amount of medicament comprises from about 0.00001 parts by weight to about 5 parts by weight based on 100 parts by weight of said carrier.

5. A method of treating a systemic disease in a patient in need thereof which comprises:

(a) administering to the patient a medicinal aerosol formulation comprising (a') a medicament present in an effective amount; (b') a fluid propellent carrier for carrying and transporting said medicament at a suitable dosing time for a suitable dosing period; and (c') a stabilizer selected from the group consisting of (1) an amino acid (2) a derivative thereof; (3) a water addition stabilizer and (4) a mixture of any of the foregoing stabilizers; and (b) maintaining the inspiratory flow rate in the patient in a range of about 0.05 to about 2 liters per second and the inspiratory volume of the patient in the range of about 0.1 to about 5 liters.

6. The method as defined in claim 4 wherein said medicament is a particulate medicament having a diameter ranging from about 1 to about 7 micrometers.

7. The method as defined in claim 4 wherein said medicament comprises a protein or *a* peptide medicament having a molecular size ranging from about 0.5 K Dalton to about 150 K Daltons.

8. The method as defined in claim 5 wherein said stabilizer comprises said water addition stabilizer.

* * * * *

UNITED STATES PATENT AND TRADEMARK OFFICE

CERTIFICATE OF CORRECTION

PATENT NO. : RE39,847 E
APPLICATION NO. : 10/219717
DATED : September 18, 2007
INVENTOR(S) : Adjei et al.

It is certified that error appears in the above-identified patent and that said Letters Patent is hereby corrected as shown below:

Column 10, line 46, in claim 1, delete “said” and insert -- and --.

Column 11, line 4, in claim 5, delete “acid” and insert -- acid, --.

Column 11, line 4, in claim 5, delete “thereof;” and insert -- thereof, --.

Signed and Sealed this
Thirty-first Day of May, 2011

David J. Kappos

David J. Kappos
*Director of the United States Patent and Trademark Office*